United States Patent
Iwasaki et al.

(10) Patent No.: US 12,403,428 B2
(45) Date of Patent: Sep. 2, 2025

(54) EVALUATION METHOD FOR PROTEIN-CONTAINING SOLUTION

(71) Applicant: ASAHI KASEI LIFE SCIENCE CORPORATION, Tokyo (JP)

(72) Inventors: Takuma Iwasaki, Tokyo (JP); Ryota Oguri, Tokyo (JP)

(73) Assignee: ASAHI KASEI LIFE SCIENCE CORPORATION, Tokyo (JP)

( * ) Notice: Subject to any disclaimer, the term of this patent is extended or adjusted under 35 U.S.C. 154(b) by 419 days.

(21) Appl. No.: 18/011,692

(22) PCT Filed: Jun. 21, 2021

(86) PCT No.: PCT/JP2021/023432
§ 371 (c)(1),
(2) Date: Dec. 20, 2022

(87) PCT Pub. No.: WO2021/261451
PCT Pub. Date: Dec. 30, 2021

(65) Prior Publication Data
US 2023/0249135 A1    Aug. 10, 2023

(30) Foreign Application Priority Data

Jun. 24, 2020    (JP) ................. 2020-108837

(51) Int. Cl.
*B01D 65/10* (2006.01)
*B01D 61/24* (2006.01)
(Continued)

(52) U.S. Cl.
CPC ....... *B01D 65/109* (2022.08); *B01D 61/2461* (2022.08); *C07K 1/34* (2013.01);
(Continued)

(58) Field of Classification Search
None
See application file for complete search history.

(56) References Cited

U.S. PATENT DOCUMENTS 9,229,009 B2    1/2016 Buhimschi et al.
2010/0015638 A1    1/2010 Uchiyama et al.
(Continued)

FOREIGN PATENT DOCUMENTS

CN    1379245 A    11/2002
CN    1845935 A    10/2006
(Continued)

OTHER PUBLICATIONS

A physicochemical investigation of membrane fouling in cold microfiltration of skim milk, T. J. Tan , * † D. Wang , * and C. I. Moraru *1, J. Dairy Sci. 97 :4759-4771 (Year: 2014).*
(Continued)

*Primary Examiner* — Krishnan S Menon
(74) *Attorney, Agent, or Firm* — Greenblum & Bernstein, P.L.C.

(57) ABSTRACT

The purpose of the present invention is to provide a method for evaluating the clogging of a filtration membrane with a protein-containing solution, including the steps of:
  a) passing a protein-containing solution through a filtration membrane,
  b) after the step a), obtaining a filtration membrane cross-section from the filtration membrane,
  c) treating the protein-containing solution before the step a), the filtration membrane before the step b), or the filtration membrane cross-section after the step b) with at least one stain specific to a protein aggregate, and
  d) confirming the presence of the protein aggregate in the filtration membrane cross-section.

18 Claims, 6 Drawing Sheets

(51) Int. Cl.
   *C07K 1/34* (2006.01)
   *G01N 21/64* (2006.01)
   *G01N 33/543* (2006.01)
   *G01N 33/68* (2006.01)

(52) U.S. Cl.
   CPC ........... *G01N 21/64* (2013.01); *G01N 33/543* (2013.01); *G01N 33/68* (2013.01); *B01D 2251/95* (2013.01); *G01N 2333/908* (2013.01); *G01N 2333/916* (2013.01)

(56) References Cited

U.S. PATENT DOCUMENTS

| | | |
|---|---|---|
| 2011/0130305 A1 | 6/2011 | Patton et al. |
| 2012/0088228 A1 | 4/2012 | Asher et al. |
| 2012/0148568 A1 | 6/2012 | Arnell et al. |
| 2013/0336981 A1 | 12/2013 | De Kruif et al. |
| 2014/0116941 A1 | 5/2014 | Thorm et al. |
| 2014/0295458 A1 | 10/2014 | Schmidt et al. |
| 2017/0028360 A1 | 2/2017 | Hamamoto et al. |
| 2017/0029462 A1 | 2/2017 | Hamamoto et al. |
| 2020/0094190 A1 | 3/2020 | Iwasaki et al. |
| 2020/0298182 A1 | 9/2020 | Futamura et al. |

FOREIGN PATENT DOCUMENTS

| | | |
|---|---|---|
| JP | 2010-14564 A | 1/2010 |
| JP | 2013-502402 A | 1/2013 |
| JP | 2014-517047 A | 7/2014 |
| JP | 2015-96855 A | 5/2015 |
| JP | 2017-195897 A | 11/2017 |
| JP | 2018-119982 A | 8/2018 |
| JP | 2019-22489 A | 2/2019 |
| WO | WO 02/01230 A2 | 1/2002 |
| WO | WO 2010/125932 A1 | 11/2010 |
| WO | WO 2015/156403 A1 | 10/2015 |
| WO | WO 2017/046552 A1 | 3/2017 |
| WO | WO 2019/173607 A1 | 9/2019 |
| WO | WO 2020/124020 A1 | 6/2020 |

OTHER PUBLICATIONS

Molecular Spectroscopic Characterization of Membrane Fouling: A Critical Review Wei Chen, 1,2 Chen Qian,2 Kang-Gen Zhou, 1 and Han-Qing Yu2,* 1492 Chem 4, 1492-1509, Jul. 12, 2018 ª 2018 Elsevier Inc (Year: 2018).*

Visualization of Protein Fouling inside a Hollow Fiber Ultrafiltration Membrane by Fluorescent Microscopy Yan Hao, Cui Liang, Akihito Moriya, Hideto Matsuyama,* and Tatsuo Maruyama* dx.doi.org/10.1021/ie302111w | Ind. Eng. Chem. Res. 2012, 51, 14850-14858 (Year: 2012).*

Characterization of protein fouling on membranes: opportunities and challenges R. Chan, V. Chen, Journal of Membrane Science 242 (2004) 169-188 (Year: 2004).*

Zhao et al., "Dye Retention Properties of CMWCNT/CaAlg Hydrogel Filtration Membrane", Journal of Tianjin Polytechnic University, 37(2):20-25 (2018) [w/ translation].

ESR for EP App. No. 21828036.0, dated Nov. 21, 2023.

ISR for PCT/JP2021/023432, dated Sep. 7, 2021 (w/ translation).

IPRP for PCT/JP2021/023432, dated Dec. 13, 2022 (w/ translation).

Iritani, "Developments of Membrane Filtration Engineering in Particle-Liquid Separation", Membrane 36(5):211-216 (2011) (w/ English Abstract).

"Immunogenicity Assessment for Therapeutic Protein Products", Guidance for Industry, U.S. Department of Health and Human Services, Aug. 2014, pp. 1-39.

* cited by examiner

1 : Trimer or higher-order oligomer
2 : Dimer
3 : Monomer

EVALUATION METHOD FOR PROTEIN-CONTAINING SOLUTION

TECHNICAL FIELD

The present invention relates to an evaluation method for a protein-containing solution.

BACKGROUND ART

Preparations having a protein as an effective ingredient, for example, plasma-derived therapies obtained from the human blood and biopharmaceuticals making use of the genetic recombination technology have recently been developed actively. These protein preparations are prepared using a raw material of biological origin and therefore contain a lot of impurities and their production steps include a multistage purification step. Purification is made using a separation method such as centrifugal separation, membrane separation, or column chromatography and among them, membrane separation is a useful means capable of separating the impurities by size.

One of the problems in membrane separation is a reduction in flux due to the clogging of a membrane during filtration. It is said that there are mainly three membrane clogging mechanisms. The first one is a phenomenon called "complete blocking" in which large particles clog the pores of a membrane. The second one is a phenomenon called "standard blocking" in which particles adsorb to the wall surface of a pore of the membrane and thereby narrow the pore. The third one is a phenomenon called "cake filtration" in which particles not so large in size are concentrated and accumulate on the membrane surface to become resistance against filtration (refer to, for example, Non-Patent Document 1). Technical experts engaged in the purification step are required to select a membrane, investigate filtration conditions, and thereby increase the efficiency of the step so as not to cause the aforesaid phenomena.

CITATION LIST

Patent Documents

Patent Document 1: Japanese Unexamined Patent Application Publication (Translation of PCT Application) No. 2014/517047
Patent Document 2: International Publication No. 2015/156403

Non-Patent Documents

Non-Patent Document 1: MEMBRANE (MEMBRANE), 36(5), 211-216 (2011)
Non-Patent Document 2: Guidance for Industry Immunogenicity Assessment for Therapeutic Protein Products (2014, U.S. Department of Health and Human Services Food and Drug Administration)

SUMMARY

Technical Problem

Proteins may form an aggregate by various stresses or stimuli. When a protein aggregate (which may hereinafter be called "aggregate", simply) is present, a large aggregate may be a cause of complete blocking of a membrane during membrane separation. A virus removing step using a virus removing membrane which step is frequently used as one of purification steps is a technology of using a membrane to separate an intended protein from a virus slightly larger than the protein. When aggregation of the intended protein occurs, the resulting aggregate may become as large as or larger than the pores of the virus removing membrane and cause the clogging of the virus removing membrane.

In addition, the aggregate is generally accompanied by denaturation. A hydrophobic amino acid residue which has been folded inside a protein molecule in native state happens to be exposed from the surface in a denatured protein. The aggregate is therefore known to easily adsorb to the surface of a hydrophobic membrane material and it may be a cause of standard blocking of the membrane.

To suppress the aggregate from blocking a membrane, it is effective to treat a solution containing the aggregate, for example, with an aggregate removing membrane upstream of the virus removing membrane.

It is known that when even a protein which has caused neither denaturation nor aggregation and thus being in native state is brought into contact with a hydrophobic surface, it adsorbs to the membrane surface by hydrophobic interaction or electrostatic interaction. In the case where this phenomenon is severe, a reduction in flux occurs due to the standard blocking of the membrane. The adsorption of the protein to the membrane surface is presumed to occur, influenced by the pH of the solution or presence of a salt. For example, when the protein and the membrane surface have charges opposite to each other, adsorption occurs due to the electrostatic interaction, but presence of an adequate amount of a salt in the solution blocks the respective surface charges and mitigates adsorption. Thus, when standard blocking occurs, adjustment of the pH or salt concentration in the filtration step with a virus removing membrane may also be effective.

Patent Document 1 discloses a method for treating a solution, which is to be filtered through a virus removing membrane, in advance by a porous polyamide-containing molded product, removing a biopolymer assembly such as protein oligomer from the solution, and thereby preventing the virus removing membrane from being clogged. Patent Document 1 however neither discloses nor suggests that clogging includes complete blocking, standard blocking, and cake filtration. Further, Patent Document 1 neither discloses nor suggests a method for confirming the presence or absence of a biopolymer assembly in the solution in advance. When no biopolymer assembly is present in the solution and the cause of the clogging of the virus removing membrane is not a biopolymer assembly like an aggregate, the clogging of the virus removing membrane may not be dissolved even by the treatment of the solution with the porous polyamide-containing molded product in advance.

Patent Document 2 discloses a method for using gold colloids different in size to determine the position at which particles of various sizes in the virus removing membrane are trapped. The method relating to Patent Document 2 however determines the pore size in the virus removing membrane only by filtering a gold colloid having a known size through the virus removing membrane and then confirming the gold colloid trapped position in the virus removing membrane. Patent Document 2 therefore neither discloses nor suggests a method for determining a cause of clogging when a protein-containing liquid whose presence of an aggregate, amount of the aggregate, size of the aggregate, shape of the aggregate, and the like are unknown is filtered through a virus removing membrane and the virus removing membrane is clogged.

An aggregate remaining in a final preparation may have a risk of affecting a side effect on patients so that the regulatory authority of each country has announced a guideline on the analysis of it. As exemplified in Non-Patent Document 2, size exclusion chromatography is thought to be a major means for analysis of an aggregate in the pharmaceutical industry and its quantitation limit is about several µg/mL. Even an aggregate present not more than this amount, however, may clog a virus removing membrane. Analytical ultracentrifugation is a technology that has recently come into use, but similar to size exclusion chromatography, it detects a protein based on ultraviolet absorbance. The quantification limit of the analytical ultrafiltration is therefore presumed to be almost equal to that of the size exclusion chromatography. Thus, in the production step of biopharmaceuticals, it is not easy to confirm whether or not a protein-containing solution particularly in a stage to be provided to a virus removing step contains an aggregate of the protein.

As described above, it is conventionally difficult to determine the cause of a clogging phenomenon which has occurred in a filtration membrane. An object of the present invention is therefore to provide a method for determining, when a filtration membrane is clogged during filtration of a protein-containing solution, whether the cause of the clogging is an aggregate or not.

Solution to Problem

The present inventors have investigated, thinking that if a membrane clogging problem occurs, it is possible to get information useful for the step improvement by knowing whether an aggregate is a cause of the clogging or not. In other words, the present inventors have found that when it becomes clear that the clogging is caused by an aggregate, the problem can be overcome, for example, by removing the aggregate in advance. The present inventors have also found that when it becomes clear that the clogging is not caused by an aggregate, the problem can be overcome by another method. When the cause of the clogging of a membrane is unknown, various measures against clogging should be taken and their inhibitory effects should be verified, respectively. However, if the cause of the clogging of a membrane becomes clear, a measure necessary for it and the effect of the measure would be predictable.

In one aspect of the present invention, there is provided a method for evaluating the clogging of a filtration membrane with a protein-containing solution, including the steps of:
a) passing a protein-containing solution through a filtration membrane,
b) after the step a), obtaining a filtration membrane cross-section from the filtration membrane,
c) treating the protein-containing solution before the step a), treating the filtration membrane before the step b), or treating the filtration membrane cross-section after the step b) with at least one stain specific to an aggregate of the protein, and
d) confirming the presence of the aggregate of the protein in the filtration membrane cross-section.

In another aspect of the present invention,
there is provided a method for evaluating the clogging of a filtration membrane with a protein-containing solution, including the steps of:
a) passing a protein-containing solution through a filtration membrane,
a-1) confirming the clogging of the filtration membrane in the step a),
b) after the step a), obtaining a filtration membrane cross-section from the filtration membrane,
c) treating the protein-containing solution before the step a), the filtration membrane before the step b), or the filtration membrane cross-section after the step b) with at least one stain specific to an aggregate of the protein, and
d) confirming the presence of the aggregate of the protein in the filtration membrane cross-section.

In a further aspect of the present invention,
there is provided a method for evaluating the clogging of a filtration membrane with a protein-containing solution, including the steps of:
a) passing a protein-containing solution through a filtration membrane,
a-2) measuring a flux in the step a),
b') when the flux has decreased, obtaining a filtration membrane cross-section from the filtration membrane,
c') adding at least one stain specific to an aggregate of the protein to the filtration membrane, and
d) confirming the presence of the aggregate of the protein in the filtration membrane cross-section.

In a still further aspect of the present invention,
there is provided a method for confirming, in a protein-containing solution, the presence of an aggregate of the protein, including the steps of:
a) passing a protein-containing solution through a filtration membrane,
b) after the step a), obtaining a filtration membrane cross-section from the filtration membrane,
c) treating the protein-containing solution before the step a), treating the filtration membrane before the step b), or treating the filtration membrane cross-section after the step b) with at least one stain specific to an aggregate of the protein, and
d) confirming the presence of the aggregate of the protein in the filtration membrane cross-section.

The aforesaid method may further include a step of washing the filtration membrane after the step a).

The aforesaid method may further include a step of washing the filtration membrane after the step c).

The aforesaid method may further include a step of washing the filtration membrane after the step c').

The aforesaid method may further include a step of adding, to the filtration membrane, a stain capable of staining both a non-aggregated protein and an aggregated protein.

The aforesaid method may further include a step of fixing the filtration membrane cross-section.

In the aforesaid method, the filtration membrane cross-section may be a cross-section of a sliced section of the filtration membrane.

In the aforesaid method, the stain specific to the aggregate may contain a material which specifically binds to an aggregation portion of the aggregate of the protein and emits fluorescence.

In the aforesaid method, the stain specific to the aggregate may be at least one selected from Nile red, Thioflavin T, and ProteoStat, and derivatives thereof.

In the aforesaid method, the stain specific to the aggregate may be a stain containing a binding material which specifically binds to the aggregation portion of the aggregate of the protein labeled with a fluorescent or luminescent material.

In the aforesaid method, the binding material which specifically binds to the aggregation portion of the aggregate of the protein may be at least one selected from an antibody, an antibody fragment, and a peptide.

In the aforesaid method, the stain specific to the aggregate may contain:

(A) a primary binding material which specifically binds to the aggregation portion of the aggregate of the protein and
(B) a secondary binding material which specifically binds to the primary binding material and contains a detectable material.

In the aforesaid method, the primary binding material may be at least one selected from an antibody, an antibody fragment, and a peptide.

In the aforesaid method, the secondary binding material may be an antibody labeled with a fluorescent material.

In the aforesaid method, the secondary binding material may be an antibody modified with an enzyme and the method may further include, after the step c), a step of adding, to the filtration membrane, a substrate which will be decomposed by an enzyme into a fluorescent or luminescent material and detecting fluorescence or luminescence.

In the aforesaid method, the secondary binding material may be an antibody modified with an enzyme and the method may further include, after the step c'), a step of adding, to the filtration membrane, a substrate which will be decomposed by an enzyme into a fluorescent or luminescent material and detecting fluorescence or luminescence.

In the aforesaid method, the enzyme may be peroxidase or alkali phosphatase.

In the aforesaid method, the filtration membrane may be a virus removing membrane.

In the aforesaid method, the step c) may be followed by the step b).

In the aforesaid method, the step c') may followed by the step b').

The aforesaid method may further include, after the step c), a step of removing an unreacted stain specific to the aggregate.

The aforesaid method may further include, after the step c'), a step of removing an unreacted stain specific to the aggregate.

In the aforesaid method, the unreacted stain specific to the aggregate may be removed by dialysis, ultrafiltration, or gel filtration.

In the aforesaid method, confirmation of the clogging of the filtration membrane in the step a) may be carried out by measuring a flux in the step a-1).

In the aforesaid method, confirmation of the clogging of the filtration membrane in the step a) may be carried out by measuring a pressure in the step a-1).

Advantageous Effects of Invention

The present invention makes it possible to provide a method for determining, when clogging of a filtration membrane occurs during filtration of a protein-containing solution, whether the clogging is caused by an aggregate or not.

DESCRIPTION OF EMBODIMENTS

The embodiment of the present invention will hereinafter be described. In the following description on the drawings, the same or similar portion is denoted by the same or similar sign. The drawing is a schematic one and does not accurately show specific dimensions and the like. The specific dimensions and the like should therefore be judged in light of the following description. There are of course included the portions whose mutual dimensional relations and ratios are different between the drawings.

The method for evaluating the clogging of a filtration membrane with a protein-containing solution according to the present embodiment includes the steps of:
a) passing a protein-containing solution through a filtration membrane,
b) after the step a), obtaining a filtration membrane cross-section from the filtration membrane,
c) treating the protein-containing solution before the step a), the filtration membrane before the step b), or the filtration membrane cross-section after the step b) with at least one stain specific to an aggregate of the protein, and
d) confirming the presence of the aggregate of the protein in the filtration membrane cross-section. The aforesaid order of the steps is not particularly limited unless otherwise specified, but it is preferred to carry out the steps in order of mention.

The method for determining the cause of the clogging of a filtration membrane with a protein-containing solution according to the present embodiment includes the steps of:
a) passing a protein-containing solution through a filtration membrane,
a-2) measuring a flux in the step a),
b') obtaining a filtration membrane cross-section from the filtration membrane when the flux decreases,
c') adding at least one stain specific to an aggregate of the protein to the filtration membrane, and
d) confirming the presence of the aggregate of the protein in the filtration membrane cross-section. The order of the aforesaid steps is not particularly limited, but it is preferred to carry out them in order of mention.

In the present embodiment, the protein is not particularly limited and examples include albumin, globulin, and fibrinogen. More preferred examples include an antibody protein. As generally defined in biochemistry, an antibody protein, one example of a physiologically active material, is a glycoprotein molecule (which may also be called "gamma globulin" or "immunoglobulin") produced by a B lymphocyte as an infection protection mechanism of vertebrates. For example, an antibody protein purified in the embodiment is used as a pharmaceutical for humans and has the substantially same structure as that of an antibody protein present in the human body to which it is administered.

The antibody protein may be either a human antibody protein or an antibody protein derived from no-human mammals such as bovines and mice. The antibody protein may also be a chimeric antibody protein with human IgG or a humanized antibody protein. The chimeric antibody protein with human IgG is an antibody protein having a variable region derived from non-human organisms such as mice and a constant region substituted by immunoglobulin derived from humans. The humanized antibody protein is an antibody protein having, in a variable region, a complementarity-determining region (CDR) derived from non-human organisms and the other framework region (FR) derived from humans. The humanized antibody protein has further less immunogenicity than that of a chimeric antibody protein.

The class (isotype) and subclass of the antibody protein is not particularly limited. For example, the antibody protein is classified into five types, IgG, IgA, IgM, IgD, and IgE, according to a difference in the structure of the constant region. The antibody protein to be purified by the filtration method according to the embodiment however may belong to any of the five classes. In the human antibody protein, IgG has four subclasses IgG1 to IgG4 and IgA has two subclasses IgA1 and IgA2. The subclass of the antibody protein to be purified by the filtration method according to the present embodiment may be any of them. The antibody protein may also include an antibody-related protein such as Fc-fusion protein in which a protein has been bound to an Fc region.

Further, the antibody protein can be classified by the source thereof. However, the antibody protein to be purified by a filtration membrane according to the present embodiment may be any of a natural human antibody protein, a recombinant human antibody protein produced by gene recombination technology, a monoclonal antibody protein, or a polyclonal antibody protein. Of these antibody proteins, preferred examples of the antibody protein to be purified by the filtration method according to the present embodiment include, but not limited to, human IgG and a monoclonal antibody from the standpoint of demand and importance as an antibody drug.

In the present embodiment, the protein-containing solution is a solution containing such a protein as exemplified above and in the production or purification procedure of the protein, the solution contains a large amount and a variety of impurities so that it is purified using a membrane separation technology.

In the present embodiment, the protein-containing solution is not particularly limited as long as the solution contains the protein in dissolved form. The type of a buffer solution usable as the solution is not particularly limited and examples include solutions containing tris, acetic acid, histidine, glycine, phosphoric acid, and citric acid, respectively.

The protein-containing solution may also contain an additive, for example, to stabilize the protein and examples of the additive include surfactants such as Tween, saccharides such as sorbitol, maltose, sucrose, and trehalose, inorganic salts such as sodium chloride and sulfonic acid salt, and amino acids such as arginine and lysine.

In the present embodiment, the concentration of the protein-containing solution is not particularly limited as long as the solution contains the protein in dissolved form. For example, the lower concentration limit of the protein-containing solution is 0.01 mg/mL or more, 0.05 mg/mL or more in another aspect, 0.1 mg/mL or more in a further aspect, 0.5 mg/mL or more in a still further aspect, 1.0 mg/mL or more in a still further aspect, and 5.0 mg/mL or more in a still further aspect. For example, the upper concentration limit of the protein-containing solution is 200 mg/mL or less, 150 mg/mL or less in another aspect, 100 mg/mL or less in a further aspect, 50 mg/mL or less in a still further aspect, and 25 mg/mL or less in a still further aspect.

In the present embodiment, the concentration of the buffer solution is not particularly limited as long as the aforesaid material to be dissolved is dissolved in the buffer solution. For example, the lower concentration limit of the buffer solution is 0.1 mmol/L or more, 1 mmol/L or more in another aspect, 10 mmol/L or more in a further aspect, 50 mmol/L or more in a still further aspect, 100 mmol/L or more in a still further aspect, and 300 mmol/L or more in a still further aspect. The buffer solution is however not necessarily used.

The concentration of the stabilizer to be added to the protein-containing solution may be determined with the protein stability or the like of the protein solution as an index. It is preferably 500 mmol/L or less or 300 mmol/L or less, more preferably 250 mmol/L or less. When the protein is sufficiently stable, the solution does not have to contain a stabilizer.

In the present embodiment, the pH of the protein-containing solution or buffer solution is not particularly limited. The lower pH limit is, for example, 3.5 or more, 4.5 or more in another aspect, 5.0 or more in a further aspect, 5.5 or more in a still further aspect, and 6.0 or more in a still further aspect. The upper pH limit is, for example, 10.0 or less, 9.0 or less in another aspect, 8.0 or less in a still further aspect, 8.5 or less in a still further aspect, 8.0 or less in a still further aspect, 7.5 or less in a still further aspect, and 7.0 or less in a still further aspect. A pH measurement method is not particularly limited and examples include methods using a hydrogen electrode, a quinhydrone electrode, an antimony electrode, and a glass electrode, respectively. Of these, the method using a glass electrode is preferred.

In the present embodiment, the filtration membrane is not particularly limited as long as it is a filtration membrane used in a step of purifying a protein from the aforesaid protein-containing solution. The filtration membrane separates impurities by size. In the membrane separation technology, impurities such as viruses are removed by passing the protein-containing solution through the inside of the membrane from one of the surfaces of the membrane to the other surface and thereby trapping the impurities inside the membrane or by passing a protein, which is an intended material, together with a liquid as a medium. The shape of the filtration membrane is not particularly limited. Examples include hollow fiber type and flat-sheet membrane type and the hollow fiber membrane is given as a preferred filtration membrane example. In another aspect, a flat-sheet membrane is also given as a preferred filtration membrane example. The material of the filtration membrane is not particularly limited and the filtration membrane may be made of a non-synthetic polymer such as regenerated cellulose or a synthetic polymer. Examples of the material of the filtration membrane include polyethersulfone, polysulfone, poly(vinylidene fluoride), cellulose, and cellulose derivatives, and mixtures thereof. The filtration membrane may be a stack of these materials or a coat of one material on another material. Further, the filtration membrane may have a surface modified by graft polymerization or a coating technique.

The filtration membrane is ordinarily formed as a filter to pass the protein-containing solution from one of the surfaces of the membrane to the other surface. The hollow fiber membrane is formed in the form of a filter as obtained, for example, by bundling a plurality of membranes, placing the bundle in a cylindrical case called "housing", and opening the end of a hollow fiber while hardening both ends with an adhesive such as polyurethane. The flat-sheet membrane is formed in the form as obtained, for example, by sandwiching the membrane between a member having an introduction port for the protein-containing solution and a member having an outlet therefor and welding the respective end portions of these members. A filtration membrane deformed into an appropriate form such as that folded into a pleat or a stacked filtration membrane may also be used as the filter.

In the present embodiment, the filtration membrane is not particularly limited, but from the viewpoint that it is designed so that a protein to be purified has a size very close to the pore size of the filtration membrane and is easily influenced by an aggregate, a membrane used for a virus removing filter is preferred. The membrane used for a virus removing filter will hereinafter be called "virus removing membrane".

In the present embodiment, the virus removing membrane is not particularly limited as long as it can substantially separate a virus from an intended protein and it is, for example, a membrane having a nominal pore size of about 15 nm or more and about 75 nm or less. For example, a membrane having a nominal pore size of 20 nm passes a protein with 150 kDa, for example, a monoclonal antibody therethrough but does not pass a parvovirus therethrough. On the other hand, for example, a membrane having a nominal pore size of 35 nm or more passes a larger protein, for example, fibrinogen with 340 kDa therethrough and removes, for example, Simian Virus 40.

In the present embodiment, the virus removing membrane has, for example, a molecular weight cut-off of 100 kD or more and 1000 kD or less. In this context, the molecular weight cut-off (MWCO) of a membrane means a nominal molecular weight cut-off (nominal molecular weight) of molecules and particles at which 90% of them pass through the membrane.

In the present embodiment, the material of the virus removing membrane is not particularly limited as long as it is a material capable of removing a virus and examples include polyethersulfone, polysulfone, poly(vinylidene fluoride), cellulose, and cellulose derivatives, and mixtures thereof.

a) Step of Passing a Protein-Containing Solution Through a Filtration Membrane

In the present embodiment, a specific aspect of passing the protein-containing solution through the filtration membrane is not particularly limited and examples include a method of feeding the protein-containing solution under pressure from one of the surfaces of the filtration membrane and passing it through the filtration membrane and a method of passing the protein-containing solution through the filtration membrane with a pump. Further, dead-end filtration by which all the amount of the protein-containing solution fed to the filtration membrane is passed therethrough or tangential flow filtration by which some of the solution is passed through the membrane and the remaining solution is returned to the original solution may be performed. The purification step of a protein is often a multistage step, but treatment may be conducted continuously after being connected to the steps before and after the filtration membrane.

Before and after the protein-containing solution is passed through the filtration membrane, a buffer solution may be passed through the filtration membrane separately from the protein-containing solution. The buffer solution may have the same properties as those of the buffer solution constituting the protein-containing solution or have properties different therefrom, but it is preferably a buffer solution having the same properties. Examples of the buffer solution are as described above. When the protein-containing solution is collected, all the amount of the protein-containing solution passed through the filtration membrane may be collected. The filtration may be performed through a plurality of filters arranged in parallel or may be performed while replacing with another one during filtration.

The amount of the protein-containing solution to be passed through the filtration membrane is not particularly limited and the lower limit is, for example, 10 L/m$^2$ and the upper limit is, for example, 1000 L/m$^2$.

As described above, the method of passing the protein-containing solution through the filtration membrane may be either the method of carrying out filtration while applying a pressure or the method of feeding the protein solution to the filtration membrane with a pump and carrying out filtration. When a pressure is applied, constant pressure filtration by which a predetermined pressure is constantly applied is preferred and it may be performed while changing the pressure according to the situation. A transmembrane pressure may be determined by time spent for the filtration or the like and the pressure is preferably not more than an upper-limit pressure recommended for the filtration membrane used. Pressures exceeding the upper limit may deform the structure of the filtration membrane, which may enable impurities such as viruses to be removed to pass through it. When filtration is performed with a pump or the like, constant rate filtration which is performed at a constant rate is preferred, but it may be performed while adjusting the flow rate of the pump so as to make constant the transmembrane pressure practically applied to the filtration membrane. The set flow rate of the pump is not limited as in the case where filtration is performed while applying a pressure and the transmembrane pressure is preferably set not to exceed the upper-limit pressure recommended for the filtration membrane.

a-1) Step of Confirming the Clogging of the Filtration Membrane in the Step a)

The method according to the present embodiment may include a step of confirming the clogging of the filtration membrane in the step a). To determine whether the filtration membrane has been clogged or not, a flux when the protein-containing solution is passed through the filtration membrane may be measured. Examples of the index of the flux include a solution amount which has passed through the filtration membrane per unit time and the unit is L/m$^2$/hour. It may be converted to a flux per unit pressure by dividing by an applied pressure. The method for measuring a flux is not particularly limited and examples include a method for measuring the amount of the protein-containing solution which has passed per unit time when it is fed under a predetermined pressure. The amount of the solution may be measured using a flowmeter or the weight or volume of the solution collected at regular intervals may be measured. In the dead-end filtration, the flow rate of the solution introduced becomes equal to the amount of the solution which passes through the membrane so that the introduction amount may be measured. When the solution is introduced into the filtration membrane at a predetermined flow rate by a pump or the like, a pressure difference (transmembrane pressure) between both surfaces of the filtration membrane may be measured. When the filtration membrane is clogged, a higher transmembrane pressure is required to pass the solution at the same flow rate so that a reduction in the flux can be found as a result of conversion into the aforesaid index. A threshold value of the flux at which the filtration membrane is determined to have caused clogging is not particularly limited as long as it is a flux which makes it practically impossible to carry out filtration. Examples include 70% or less relative to the flux immediately after filtration is started and 50% or less in another aspect. For example, when the measured value of the flux of the filtration membrane is not more than the threshold value of the flux, the filtration membrane is determined to have caused clogging.

To determine whether the filtration membrane has caused clogging or not, a filtration pressure under which the protein-containing solution is passed through the filtration membrane may be measured. An increase in filtration pressure may be found by measuring the transmembrane pressure as described above.

a-2) Step of Measuring a Flux in the Step a)

The method according to the present embodiment may include a step of measuring a flux in the step a). A flux when the protein-containing solution is passed through the filtration membrane is measured to determine whether the filtration membrane has caused clogging or not. Examples of the index of the flux include the amount of the solution which passes through the filtration membrane per unit time and the unit is L/m$^2$/hour. It may be converted to a flux per unit pressure by dividing by an applied pressure. The method for measuring a flux is not particularly limited and examples include a method for measuring the amount of the protein-containing solution which has passed per unit time when it is fed under a predetermined pressure. The amount of the solution may be measured using a flowmeter or the weight or volume of the solution collected at regular intervals may be measured. In the dead-end filtration, the flow rate of the solution introduced becomes equal to the amount of the solution which passes through the membrane so that an introduction amount may be measured. When the solution is introduced into the filtration membrane at a predetermined flow rate by a pump or the like, a pressure difference (transmembrane pressure) between both surfaces of the filtration membrane may be measured. When the filtration membrane is clogged, a higher transmembrane pressure is required to pass the solution at the same flow rate so that a reduction in the flux can be found as a result of conversion into the aforesaid index. A threshold value of the flux at which the filtration membrane is determined to have caused clogging is not particularly limited as long as it is a flux which makes it practically impossible to carry out filtration. Examples include 70% or less relative to the flux immediately after filtration is started and 50% or less in another aspect. For example, when the measured value of the flux of the filtration membrane is not more than the threshold value of the flux, the filtration membrane is determined to have caused clogging.

b) Step of Obtaining a Filtration Membrane Cross-Section from the Filtration Membrane after the Step a)

After the step a), in order to confirm whether or not the clogging of the filtration membrane occurs due to an aggregate, the filtration membrane which has caused clogging is collected and the presence or absence of the aggregate inside the filtration membrane is confirmed. In observing the inside of the filtration membrane, the cross-section of a fragment obtained from the filtration membrane may be observed. The fragment is obtained from the filtration membrane, for example, by cutting the filtration membrane with a cutter such as razor but a cutting method is not particularly limited. It is preferred to use a sharp cutter to keep the cross-sectional structure or the state of particles which have remained inside as much as possible. In a hollow fiber filtration membrane, the fragment of the filtration membrane can be obtained by perpendicularly cutting the hollow fiber membrane in the fiber length direction. When the filtration membrane is a flat-sheet membrane, the fragment of the filtration membrane can be obtained by cutting the filtration membrane perpendicularly to the membrane surface. When the filtration membrane is hard to cut due to very small thickness or the like, the filtration membrane may be embedded in an embedding agent such as paraffin or resin and then the resulting filtration membrane may be sliced with a tool such as microtome. The membrane may be sliced into a thickness of preferably 2 μm or more and 20 μm or less, more preferably 4 μm or more and 10 μm or less. The fragment of the filtration membrane may also be obtained by cooling the filtration membrane to a very low temperature with liquid nitrogen or the like and then cleaving the resulting filtration membrane.

b') Step of Obtaining a Filtration Membrane Cross-Section from the Filtration Membrane in the Case where a Flux has Decreased In the case where it is judged that the flux has decreased in the step a-2) and the filtration membrane has caused clogging, the filtration membrane which has caused clogging is collected and the presence or absence of an aggregate inside the filtration membrane is confirmed, in order to confirm whether or not the cause of the clogging of the filtration membrane is the aggregate. In observing the inside of the filtration membrane, the cross-section of a fragment obtained from the filtration membrane may be observed. The fragment is obtained from the filtration membrane, for example, by cutting the filtration membrane with a cutter such as razor but a cutting method is not particularly limited. It is preferred to use a sharp cutter to keep the cross-sectional structure or the state of particles which have remained inside as much as possible. In a hollow fiber filtration membrane, the fragment of the filtration membrane can be obtained by perpendicularly cutting the hollow fiber membrane in the fiber length direction. When the filtration membrane is a flat-sheet membrane, the fragment of the filtration membrane can be obtained by cutting the filtration membrane perpendicularly to the membrane surface. When the filtration membrane is hard to cut due to very small thickness or the like, the filtration membrane may be embedded in an embedding agent such as paraffin or resin and then the resulting filtration membrane may be sliced with a tool such as microtome. The membrane may be sliced into a thickness of preferably 2 μm or more and 20 μm or less, more preferably 4 μm or more and 10 μm or less. The fragment of the filtration membrane may also be obtained by cooling the filtration membrane to a very low temperature with liquid nitrogen or the like and then cleaving the resulting filtration membrane.

c) Step of Treating the Protein-Containing Solution Before the Step a), Treating the Filtration Membrane Before the Step b), or Treating the Filtration Membrane Cross-Section after the Step b) with at Least One Stain Specific to an Aggregate of the Protein The following staining treatment is performed to confirm whether or not an aggregate is present in the filtration membrane. For example, by adding a stain specific to an aggregate of the protein to the protein-containing solution before the step a), the aggregate of the protein in the solution can be subjected to staining treatment. An adequate amount of the stain may be added to the protein-containing solution before filtration through the filtration membrane. By adding the stain specific to the aggregate of the protein to the filtration membrane in advance before the step b), the aggregate of the protein trapped in the filtration membrane can be subjected to staining treatment. Instead, by adding the stain specific to the aggregate of the protein to the filtration membrane cross-section after the step b), the aggregate of the protein trapped in the filtration membrane can be subjected to staining treatment. The addition of the stain to the filtration membrane cross-section simultaneously while obtaining the filtration membrane fragment may also be included in the treatment of the filtration membrane cross-section with the stain after the step b).

c') Step of Adding at Least One Stain Specific to an Aggregate of the Protein to the Filtration Membrane The presence or absence of an aggregate in the filtration membrane is confirmed by staining the filtration membrane with a stain specific to an aggregate of the protein. The step c') may be performed, for example, after the step b'). In this case, the cross-section of the filtration membrane fragment obtained in the step b') is stained with the stain specific to an aggregate and then, whether or not the filtration membrane cross-section is stained is observed. Instead, the step c') may be followed by the step b'). In this case, the stain specific to an aggregate may be added to the filtration membrane before the fragment is obtained. Then, the step b') is performed to obtain the fragment of the filtration membrane and whether or not the filtration membrane cross-section is stained is observed.

In the step c) or c'), the stain specific to an aggregate of the protein specifically stains the aggregate of the protein but does not stain a non-aggregated protein. Examples of such a stain include common reagents such as Thioflavin T and Nile red and Detection reagent included in a ProteoStat aggregate assay kit marketed by ENZO LIFESCIENCES. For example, protein aggregate-specific stains described in WO03/000853 or WO2011/065980 are usable. These stains are compounds which recognize a specific hydrophobic region on the surface of an aggregate as an aggregation portion, bind to the region, and emit fluorescence. The amount or conditions of the stain to be used differ, depending on the reactivity of each product or the like or depending on the amount of the aggregate contained in the filtration membrane. Each stain is preferably added in a large excess relative to the aggregate and at the same time in such an amount that the background fluorescence does not become a problem. It is preferred to set the amount or conditions of the stain so that a clear difference appears between a signal intensity when an aggregate-free negative control sample is stained and a signal intensity when an aggregate-containing positive control sample is stained. The term "clear difference" means that when the gray value of the image obtained is checked, the signal intensity of the positive control sample is, for example, 5 times or more, preferably 10 times or more the signal intensity of the negative control sample, though the difference is not particularly limited thereto.

As another example of the stain specific to an aggregate, there are antibodies, antibody fragments, and peptides, each having specific affinity for the aggregate and binding to the aggregate. For example, protein aggregate-specific stains described in Anal. Chem. 2016, 88, 10095-10101 may be used. Since antibodies, antibody fragments, peptides, and the like do not emit a signal, they may be directly labeled with a fluorescent material or the like. Secondary binding materials such as fluorescence-labeled antibodies which specifically bind to primary binding materials, such as antibodies, antibody fragments, and peptides, having specific affinity for the aggregate, may also be used. Further examples of the stain specific to an aggregate include antibodies labeled with an enzyme such as alkali phosphatase or peroxidase. A signal may be obtained by adding the enzyme to the filtration membrane cross-section to react it with the aggregate and then adding a material which emits a signal by an enzyme-induced reaction. Whichever stain is used, it is preferred to wash off the excess stain from the filtration membrane and then observe the filtration membrane cross-section in order to prevent detection of an extra signal. In addition, by covering the exposed filtration membrane cross-section with a blocking agent before staining to suppress a non-specific reaction between the stain and the filtration membrane cross-section, the stain may be suppressed from being adsorbed to the filtration membrane cross-section and thereby non-specifically staining the filtration membrane. Any material can be used as the blocking agent as long as it adsorbs to the filtration membrane cross-section to cover the filtration membrane cross-section therewith and is inert to the stain. Examples include proteins such as BSA, serum, and skim milk, protein-free products such as those sold under the trade name of BlockPro and Stabilblot, and mixed agents thereof such as those sold under the trade name of BlokingOne. In particular, non-protein blocking agents are developed to block a membrane used for western blotting or the like so that they may be suited for use in the blocking of the filtration membrane, which is a similar polymer membrane.

Specific staining of the aggregate may be carried out more accurately by conducting a step of washing the filtration membrane after filtration and thereby removing the extra protein from the filtration membrane. Examples of the washing liquid include protein-free water and various buffer solutions. The washing liquid is preferably a buffer solution same as that used as the medium of the protein-containing solution because it can keep the state of the filtration membrane and at the same time, can retain the adsorbed material or the like in the filtration membrane. The filtration membrane may be washed by filtration washing, that is, washing the filtration membrane with the washing liquid, by soaking the filtration membrane in the washing liquid, or by directly pouring the washing liquid to the filtration membrane cross-section. The washing method of the filtration membrane is not particularly limited but filtration washing is preferred because it can wash the membrane by allowing the washing liquid to penetrate even in the pore of the filtration membrane.

Specific staining of the aggregate may also be carried out more accurately by subjecting the filtration membrane after filtration to fixing treatment and thereby fixing proteins or particles remaining inside the membrane. For fixing, a technique used for a staining technique in a common biological experiment can be used and examples include a method of using an aldehyde such as formaldehyde or glutaraldehyde and a method using an organic solvent such as ethanol or acetone. When fixing treatment is performed, a fixing agent is preferably washed to prevent it from having an influence on the subsequent staining. In the fixing treatment with an aldehyde, activation treatment may be performed before staining to relax the fixing treatment to some extent and thereby improve the reactivity with the stain. A solvent used for the fixing treatment or the subsequent washing or activation is not limited and common buffer solutions such as phosphate buffer solution (PBS) are preferred. To enhance the washing efficiency, a trace amount of a surfactant such as Tween 20 or Tween 80 may be added to the buffer solution.

d) Step of Confirming the Presence of the Aggregate in the Filtration Membrane Fragment If after the treatment with the stain specific to an aggregate, a signal of the stain is found in the observed filtration membrane cross-section, the aggregate is present in the filtration membrane. The protein-containing solution therefore contains the aggregate of the protein, from which it can be determined that the clogging with it may be a cause of the clogging. On the other hand, if no signal of the stain is found in the observed filtration membrane cross-section, no aggregate of the protein is present in the filtration membrane, from which it can be determined that no clogging due to the aggregate has occurred. When it is found that clogging with the aggregate has occurred, pre-filtration treatment for removing the aggregate may be performed upstream of the filtration membrane or a buffer solution difficult to cause aggregation may be selected based on the study on the stability of an intended protein. Thus, by selecting a measure capable of preventing the aggregate from affecting on the filtration membrane in the filtration step (particularly, a virus removing step) in the biopharmaceutical production, the filtration of the protein-containing solution through the filtration membrane can be performed without clogging. On the other hand, when it is found that clogging has occurred but is not caused by the aggregate, the cause of the clogging is presumed to be an intended protein adsorbed to the pore wall of the filtration membrane so that a buffer solution capable of suppressing the adsorption of the intended protein or a measure such as changing the material of the filtration membrane may be selected.

Not only the stain specific to an aggregate but also a stain capable of staining all the proteins including an aggregate and a non-aggregated protein may be added to the filtration membrane and the protein and the aggregate thereof may be observed simultaneously. Addition of this step makes it possible to confirm that, when the aggregate is not contained, a protein which has been neither denatured nor aggregated adsorbs to the filtration membrane and narrows the pore. Staining with the stain capable of staining all the proteins may be performed before or after the step c) or the step c'), or simultaneously. These two stains may be selected so that they can be distinguished from each other. Fluorescent stains may be selected so that they differ in excitation wavelength or fluorescence wavelength. The stain capable of staining all the proteins is not particularly limited as long as it can achieve the aforesaid purpose. Examples include antibodies which specifically bind to the intended protein and to which a coloring matter has bound. When a large amount of proteins adsorb to the filtration membrane, the fluorescence derived from the aromatic amino acid which the proteins adsorbing to the filtration membrane have may be detected.

Therefore, by the method according to the present embodiment, the presence of an aggregate in the protein-containing solution can be confirmed and the method contributes to, for example, an improvement in the efficiency of a production step of biopharmaceuticals.

Whether or not a protein-containing solution contains enough aggregate to cause clogging of a filtration membrane becomes clear for the first time after practical filtration so that the method according to the present embodiment is preliminarily performed in a scale smaller than an intended scale and then filtration may be performed in a large scale. In the preliminary test, a protein-containing solution mixed in advance with a stain specific to the aggregate may be filtered through a filtration membrane, followed by observation of the filtration membrane cross-section. Even if the stain specific to an aggregate is mixed with the protein-containing solution, no signal is detected in the filtration membrane cross-section when the amount of the aggregate is trace, but a signal can be detected in the filtration membrane cross-section when the aggregate is accumulated in the filtration membrane enough to cause clogging of the filtration membrane. Preliminary mixing of the stain specific to an aggregate with the protein-containing solution enables to omit the staining step to be conducted after the filtration. In this case, however, the stain not reacting with the aggregate may remain in the filtration membrane so that sufficient washing of the filtration membrane is preferred. From the standpoint of preventing a non-specific reaction between the stain and the filtration membrane, it is preferred to add the stain to the protein-containing solution, remove the stain which has not bound to the aggregate from the protein-containing solution by dialysis treatment or the like, and then filter the protein-containing solution.

EXAMPLES

The present embodiments will hereinafter be described in detail based on Examples and Comparative Examples. The present invention is not limited to or by the following Examples, but can be performed in any mode without departing from the gist of the present invention.

1. Preparation of a Protein-Containing Solution Containing an Aggregate

To confirm whether or not the aggregate of a protein can be stained specifically by a stain, the aggregate of a protein was prepared artificially by acid treatment and a model filtration experiment was performed.

With a human immunoglobulin preparation (Donation Venoglobulin IH 5% I.V., Japan Blood Products Organization), 200 mL of a solution having a globulin final concentration of 2% and a sodium chloride concentration of 100 mmol/L was prepared. The resulting solution had a pH of 4.5 and an average diameter of the particles contained in the solution was 11.8 nm when subjected to a dynamic light scattering method. After the solution was reduced to pH 2.5 with a 1 mol/L aqueous hydrochloric acid solution at a room temperature and allowed to stand for 1 hour, the resulting solution was returned to pH 4.5 with a 1 mol/L aqueous sodium hydroxide solution and allowed to stand for 24 hours to obtain a human immunoglobulin-containing solution (which may hereinafter be called "Solution A") containing a globulin aggregate.

Figure 1:
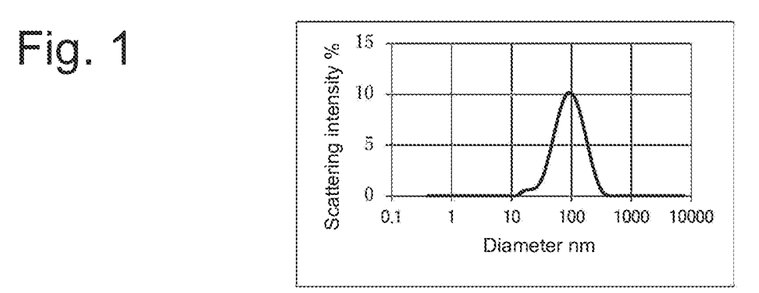
FIG. 1 is a graph showing the measurement results of dynamic light scattering of an artificially-prepared protein aggregate solution.

As a result of measurement of the average diameter of the particles contained in Solution A by the dynamic light scattering method, the average diameter was 74.3 nm. For the measurement, ZetaSizer Nano, product of Malvern Panalytical was used. The results are shown in FIG. 1. The light intensity at the time of measurement (attenuation conditions of irradiation light), a distance from a light source, and a total measurement time (cumulative number and measurement time per cumulative number) were set using an automatic setting function of the system. The measurement temperature was 25.0° C. and the measurement angle was 173°.

Figure 2:
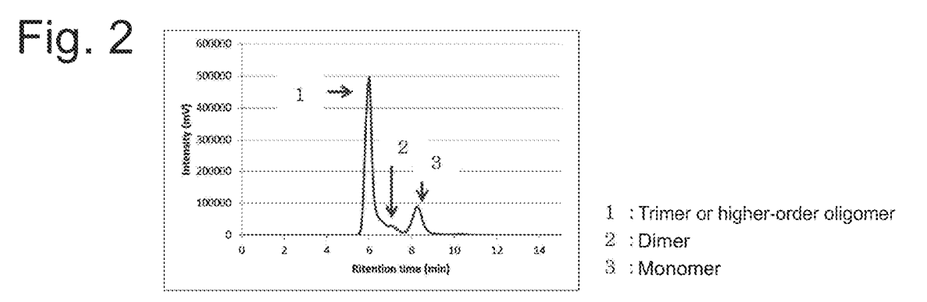
FIG. 2 is a graph showing the size exclusion chromatography results of an artificially-prepared protein aggregate solution.

As a result of the size exclusion chromatographic analysis of Solution A, it contained 16.5% of a monomer, 5.6% of a dimer, and 77.8% of a trimer or higher-order oligomer, each in terms of a relative area ratio calculated from the peak area of the chart thus obtained. In the present Example, a model experiment was performed by preparing an oligomer-containing solution and adding it to a protein solution so that the average diameter of a sample fractionated by the size exclusion chromatographic analysis was not measured. For the size exclusion chromatography, used were a high-performance liquid chromatograph (Prominence, product of Shimadzu Corporation) and a column (TSK gel G3000SWXL, product of TOSOH, exclusion limit molecular weight: 500,000 Da). The mobile phase contained a 0.3 mol/L phosphate buffer with pH 6.9, 0.2 mol/L arginine-HCl, and 0.1 mol/L of NaCl. The measurement temperature was 25° C., measurement time was 20 minutes, and flow rate was 1.0 mL/min. One example of the measurement results is shown in FIG. 2. In FIG. 2, Peak 1 represents a globulin trimer or higher-order oligomer, Peak 2 represents a globulin dimer, and Peak 3 represents a monomer. Thus, Solution A was confirmed to be a protein-containing solution containing an aggregate. Respective ratios of the monomer and the oligomers were calculated from the peak area of the chromatography chart and used as a relative area ratio. The same will be applied to the following Examples and the concentration of the monomer and oligomers is expressed by a relative area ratio %.

Figure 3:
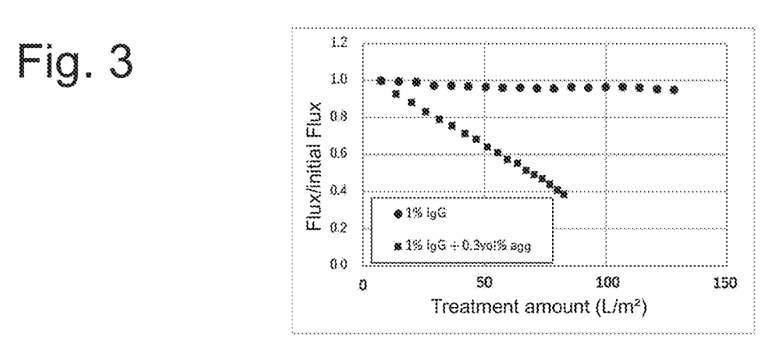
FIG. 3 is a graph showing, when each of a solution containing a protein aggregate and a solution not containing a protein aggregate are filtered through a virus removing filter, the relation between a treatment amount and a flux.

2. Confirmation of the Clogging by Filtering a Protein-Containing Solution Containing an Aggregate Through a Filtration Membrane 2-1 Confirmation of the Clogging of a Filtration Membrane A human immunoglobulin preparation (Donation Venoglobulin IH 5% I.V., Japan Blood Products Organization) was diluted with distilled water for injection (Otsuka Pharmaceutical), followed by the addition of sodium chloride to give a 300 mL solution having a globulin concentration of 1% and a sodium chloride concentration of 100 mmol/L. The resulting solution was divided into two and 0.29 mL of Solution A was added to one of the two solutions so that it contained 0.3% of a globulin trimer or higher-order oligomer. The solutions thus obtained were subjected to constant pressure dead-end filtration at 98 kPa by using Planova 20N (trade mark, product of Asahi Kasei Medical), a virus removing filter equipped with a hollow fiber membrane. The membrane area of the filter used is 0.001 m$^2$. The weight of the filtrate was measured and the flux was calculated with the passage of time. To compare the clogging degree precisely, a ratio of the initial flux to the flux at each measurement point was determined. The results are shown in FIG. 3. A sample to which no aggregate was added did not cause clogging. On the other hand, the aggregate-added sample caused clogging.

Figure 4:
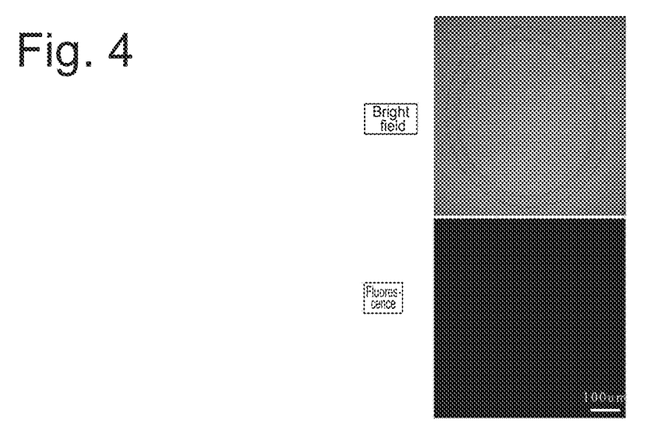
FIG. 4 is a fluorescence microscopic observation image showing that a virus removing filter before use is not stained with a stain specific to the aggregate.
Figure 5:
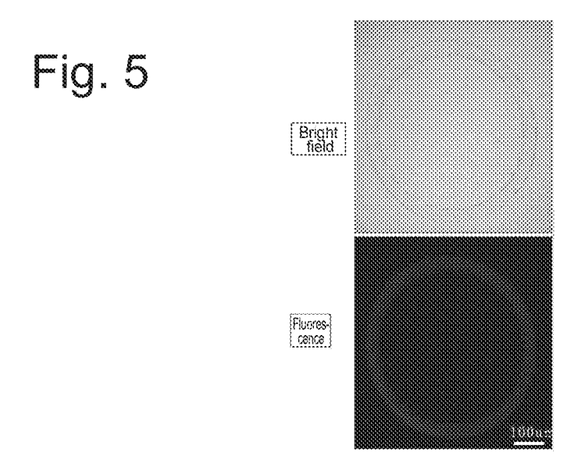
FIG. 5 is a fluorescence microscopic observation image showing that a virus removing filter through which an aggregate-free globulin solution has been filtered is not stained with a stain specific to an aggregate.
Figure 6:
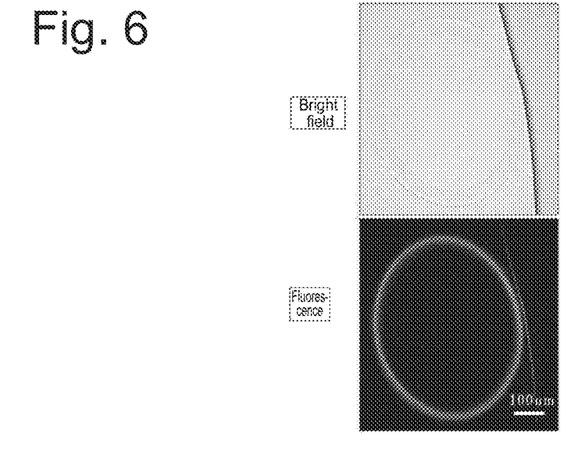
FIG. 6 is a fluorescence microscopic observation image showing that a virus removing filter through which an aggregate-containing solution has been filtered is stained with a stain specific to the aggregate.

2-2 Confirmation of the Presence of an Aggregate in the Clogged Filtration by Using a Stain Specific to an Aggregate After the virus removing filter used for filtration was subjected to filtration washing with water, the hollow fiber membrane was taken out from the filter, soaked in a 4% paraformaldehyde phosphate buffer solution (FUJIFILM Wako Pure Chemical Corporation), and fixed. After the hollow fiber membrane was soaked and washed in PBS to wash off paraformaldehyde, cut into about 5 mm, and cryoembedded at −20° C. with an OCT compound (Sakura Finetek), a 8-µm thin section of the hollow fiber membrane was obtained using a cryomicrotome (CM1950, Leica Biosystems). The compound was washed with water and then with PBS and soaked in a PBS-T solution containing 2% BSA at room temperature for 10 minutes for blocking. After washing, a stock solution of a stain included in a ProteoStat protein aggregation measurement assay kit (Enzo life sciences) was diluted to 1000 times with a buffer solution attached to the kit and the resulting diluted solution was added to the section of the hollow fiber membrane. After they were reacted at room temperature for 40 minutes, the section was washed to remove the excess stain. Each washing was performed four times with 0.05% Tween 20-containing PBS (which will hereinafter be abbreviated as "PBS-T"). For a blank experiment, a section subjected to a similar treatment with Planova 20N (trade mark, product of Asahi Kasei Medical) through which nothing was filtered was prepared. The sections thus obtained were each observed using the system of Leica (DM18 fluorescence microscope, LASX software). For the fluorescence observation, used were a 472/30-nm excitation filter, a 598/25-nm fluorescence filter, and 598-nm dichroic mirror. Observation conditions such as irradiation time were controlled to have a sufficient gray value in the aggregate-containing sample and thus, all the samples were observed. A microscopic observation image was taken by a CMOS monochrome microscope camera (Leica, DFC9000) as a 16-bit tiff format file. Each image was incorporated in ImageJ (ver 1.52a) and observation results indicated without control of the contrast of gray value are shown in FIG. 4 to FIG. 6. From the filter through which nothing was filtered, a fluorescence signal larger than the background fluorescence was not observed as shown in FIG. 4. From the filter through which the sample to which no aggregate was added was filtered, a fluorescence signal larger than the background fluorescence was not observed as shown in FIG. 5. From the filter through which the aggregate-added sample was filtered, a fluorescence signal larger than the background fluorescence was observed as shown in FIG. 6. It has therefore been confirmed that by the method according to the present Example, the stain does not react with a non-aggregated globulin and only a globulin aggregate can be detected.

Figure 7:
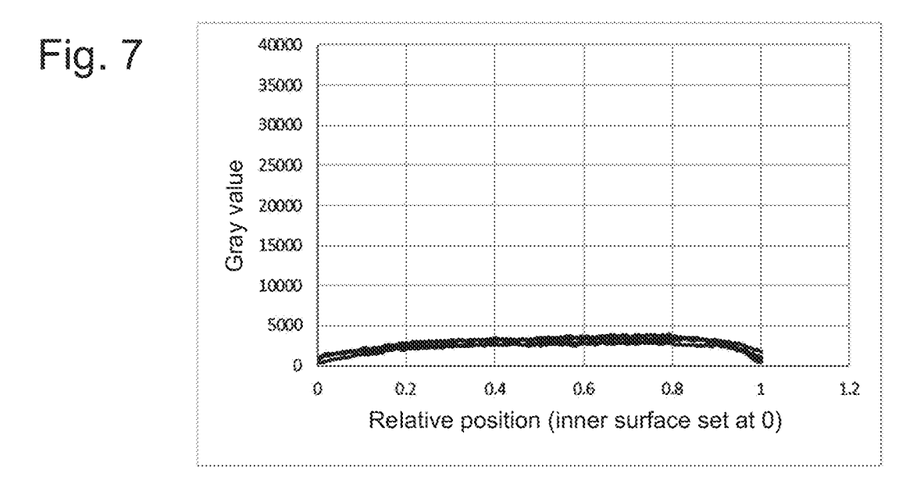
FIG. 7 is a line profile of a fluorescence intensity in the membrane thickness direction of the fluorescence microscopic observation image shown in FIG. 4. A relative position with an inner surface set at 0 and an outer surface set at 1 is plotted along the abscissa and a gray value at the relative position is plotted along the ordinate.
Figure 8:
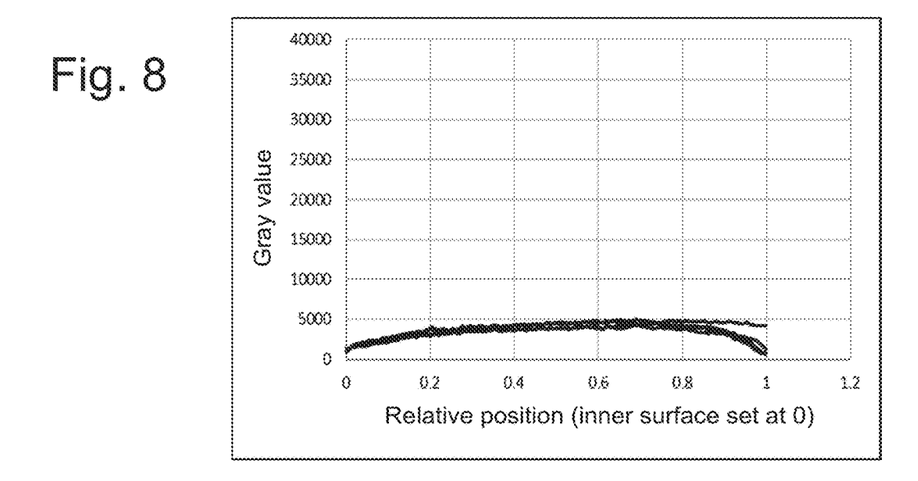
FIG. 8 is a line profile of a fluorescence intensity in the membrane thickness direction of the fluorescence microscopic observation image shown in FIG. 5. A relative position with an inner surface set at 0 and an outer surface set at 1 is plotted along the abscissa and a gray value at the relative position is plotted along the ordinate.
Figure 9:
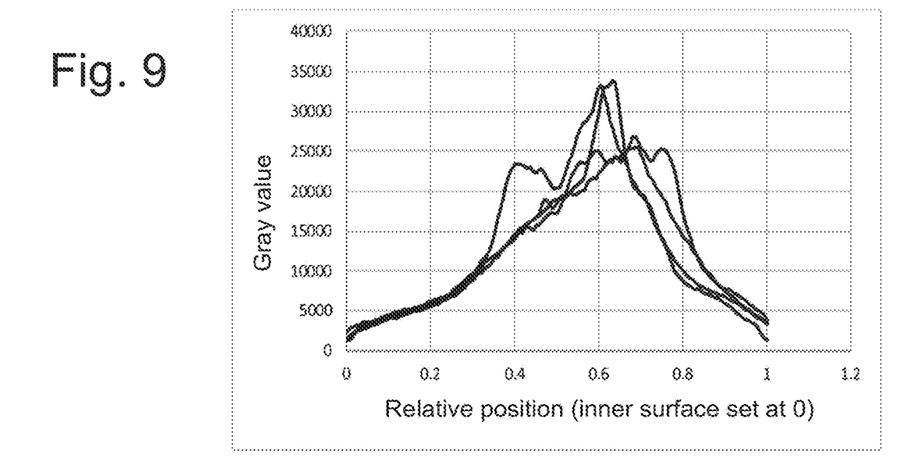
FIG. 9 is a line profile of a fluorescence intensity in the membrane thickness direction of the fluorescence microscopic observation image shown in FIG. 6. A relative position with an inner surface set at 0 and an outer surface set at 1 is plotted along the abscissa and a gray value at the relative position is plotted along the ordinate.

Indication results of the line profile of gray value from the inner surface to the outer surface at four places of each image by using ImageJ are shown in FIG. 7 to FIG. 9. The gray value of the filter through which nothing was filtered was low as shown in FIG. 7. The gray value of the filter through which the sample to which no aggregate was added was filtered was low as shown in FIG. 8. The gray value of the filter through which the aggregated-added sample was filtered was high and characteristic peaks appeared as shown in FIG. 9. The site at which the peak was detected can be regarded as a region where an aggregate is trapped. The aforesaid findings have revealed that even if an aggregate which is a trimer or higher-order oligomer is present in an amount as small as 0.3%, use of the method according to the present Example enables detection of the aggregate and distinguishment of an aggregate-having membrane from an aggregate-free membrane.

Example 1

Using a human immunoglobulin preparation (Donation Venoglobulin IH 5% I.V., obtained from Japan Blood Products Organization), 200 mL of a protein-containing solution diluted into a globulin concentration of 3% with a citrate phosphate buffer having pH 4.0 was prepared. As the citrate phosphate buffer, used was a solution obtained by adjusting a McIlvaine buffer solution (10× concentration) (product of Nacalai Tesque) so that the final concentration be 20-fold dilution of a stock solution. The resulting solution was divided into two and sodium chloride was added to one of the solutions to give a sodium chloride concentration of 30 mmol/L (Example 1-1) and to the other solution to give a sodium chloride concentration of 190 mmol/L (Example 1-2). The solutions thus obtained were subjected to 98 kPa constant pressure dead-end filtration for 5 hours by using Planova 20N (trade mark, product of Asahi Kasei Medical) equipped with a hollow fiber membrane having a membrane area of 0.001 m$^2$. A flux per unit area and per unit time for a period from 5 minutes to 10 minutes after the filtration was started and further, a ratio (which will hereinafter be called "flux ratio") of the aforesaid flux to a flux in the last 5 minutes was calculated. The results are shown in Table 1. In Example 1-1, the flux ratio was 0.87, showing that a reduction in flux was slight, while in Example 1-2, the flux ratio was 0.71 and the clogging degree of the hollow fiber membrane was large.

Figure 10:
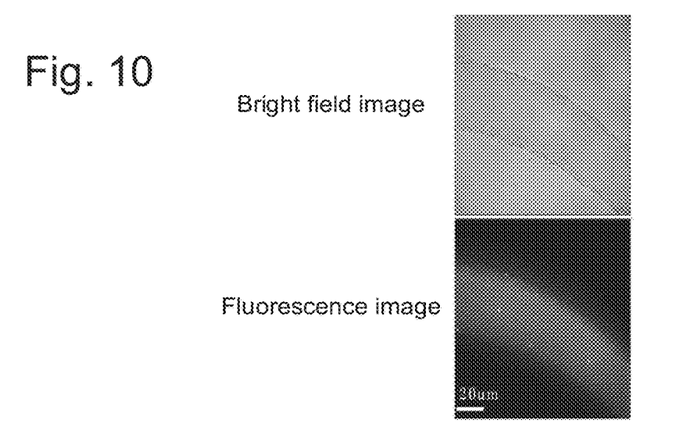
FIG. 10 is a fluorescence microscopic observation image of a virus removing filter stained with the stain specific to the aggregate according to Example 1-1.
Figure 11:
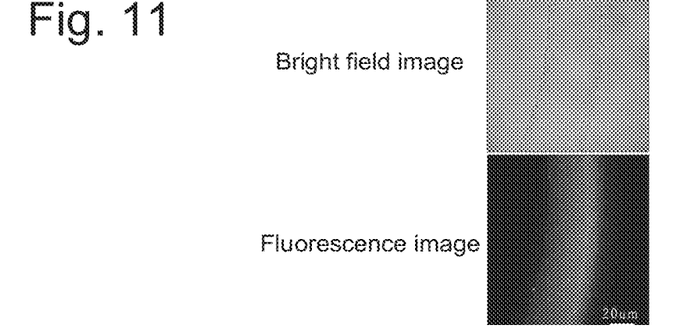
FIG. 11 is a fluorescence microscopic observation image of a virus removing filter stained with the stain specific to the aggregate according to Example 1-2.
Figure 12:
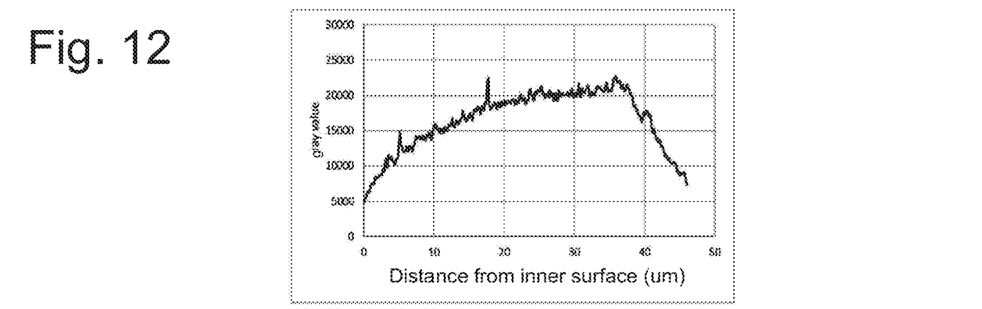
FIG. 12 is a line profile of a fluorescence intensity in the membrane thickness direction of the fluorescence microscopic observation image shown in FIG. 10. A distance from the inner surface is plotted along the abscissa and a gray value is plotted along the ordinate.
Figure 13:
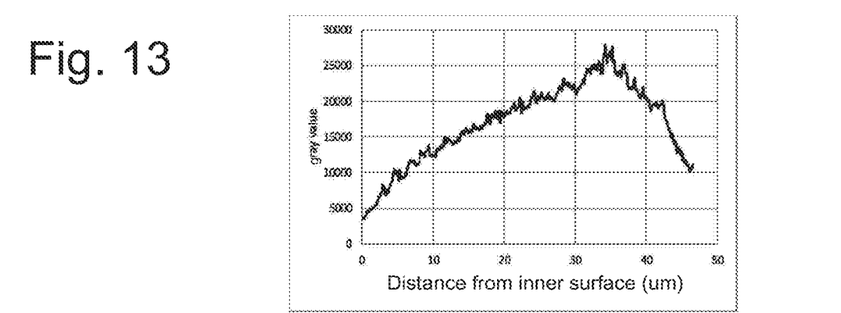
FIG. 13 is a line profile of a fluorescence intensity in the membrane thickness direction of the fluorescence microscopic observation image shown in FIG. 11. A distance from the inner surface is plotted along the abscissa and a gray value is plotted along the ordinate.

The hollow fiber membrane after the filtration was collected, stained, at the cross-section thereof, by a procedure similar to that described above in 2-2, and observed with a 100× oil-immersion objective lens. The image of the membrane cross-section is shown in FIG. 10 and FIG. 11. The line profile graphs obtained from the images are shown in FIG. 12 and FIG. 13. As shown in FIG. 10 and FIG. 12, in Example 1-1, only a signal thought to be the background fluorescence was detected as in FIG. 5. On the other hand, as shown in FIG. 11, from the fluorescence microscopic observation image of Example 1-2, a portion emitting a streaky strong signal was observed particularly in the vicinity of the outer surface. As shown in FIG. 13, in the line profile, a high intensity was confirmed in a region in the vicinity of the outer surface compared with Example 1-1. The aforesaid findings have revealed that a reduction in flux in Example 1-2 in which clogging occurred was caused by an IgG aggregate formed due to a high sodium chloride concentration.

TABLE 1

| | Example 1-1 | Example 1-2 | Example 2 |
|---|---|---|---|
| Solution pH | 4.0 | 4.0 | 7.0 |
| Sodium chloride concentration (mmol/L) | 30 | 190 | 30 |
| IgG concentration (%) | 3.0 | 3.0 | 3.0 |
| Flux ratio | 0.87 | 0.71 | 0.31 |

Example 2

Figure 14:
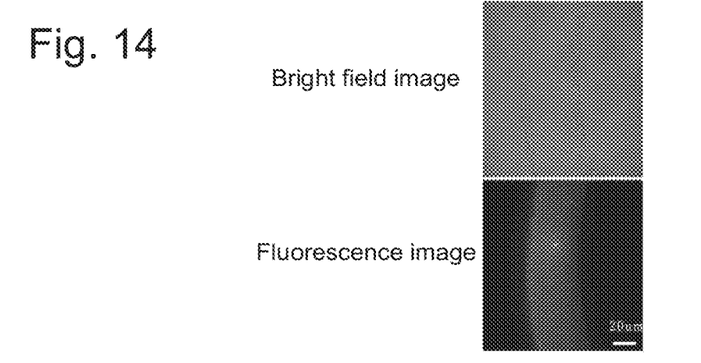
FIG. 14 is a fluorescence microscopic observation image of a virus removing filter stained with the stain specific to the aggregate according to Example 2.
Figure 15:
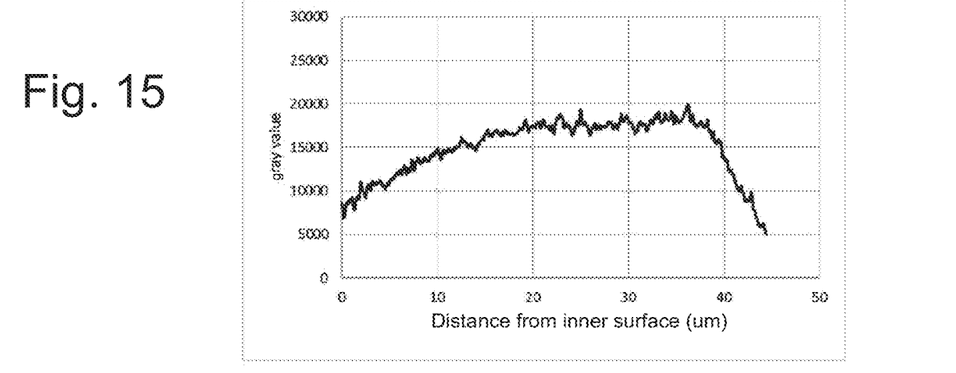
FIG. 15 is a line profile of a fluorescence intensity in the membrane thickness direction of the fluorescence microscopic observation image shown in FIG. 14. A distance from the inner surface is plotted along the abscissa and a gray value is plotted along the ordinate.

In a manner similar to that of Example 1 except the pH of the buffer solution was set at 7.0, a protein-containing solution was prepared. Sodium chloride was added to the resulting solution to give 30 mmol/L and thus, a solution of Example 2 was obtained. The solution of Example 2 was subjected to constant pressure dead-end filtration at 98 kPa for 5 hours using Planova 20N (trade mark, product of Asahi Kasei Medical) having a membrane area of 0.001 m$^2$. A flux ratio of the solution of Example 2 calculated as in Example 1 is 0.31 as shown in Table 1, revealing that severe clogging occurred in the hollow fiber membrane. The cross-section of the hollow fiber membrane used was stained and observed as in Example 1 and the results are shown in FIG. 14. The line profile obtained from the image is shown in FIG. 15. A place having a fluorescence intensity higher than the background fluorescence was not observed from the fluorescence image and even from the line profile, no strong signal was detected. The aforesaid results have shown that the cause of the clogging which occurred by the filtration of Example 2 was not an aggregate.

Comparative Example 1

Figure 16:
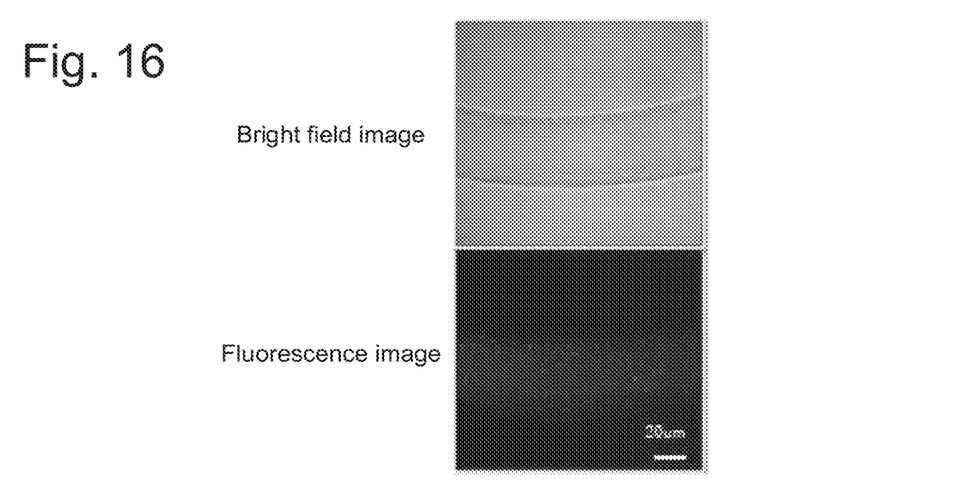
FIG. 16 is a fluorescence microscopic observation image of a virus removing filter stained with the fluorescence-labeled anti-globulin antibody according to Comparative Example 1-1.
Figure 17:
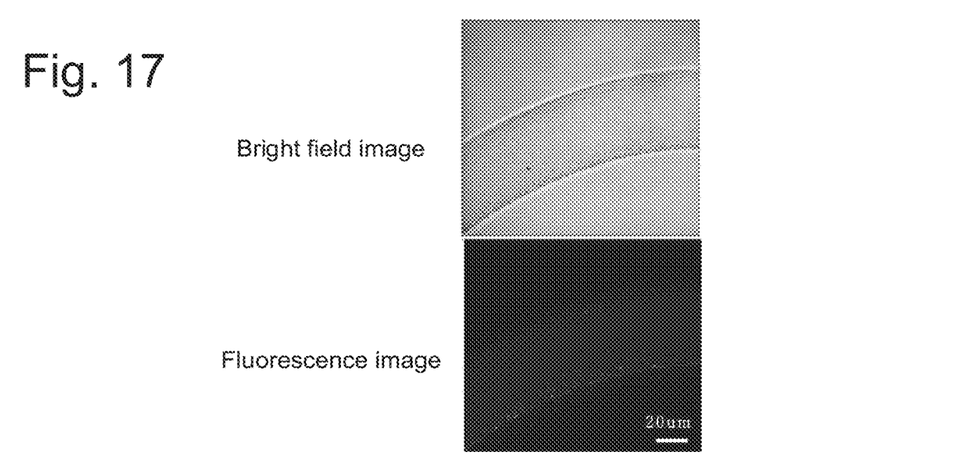
FIG. 17 is a fluorescence microscopic observation image of a virus removing filter stained with the fluorescence-labeled anti-globulin antibody according to Comparative Example 1-2.
Figure 18:
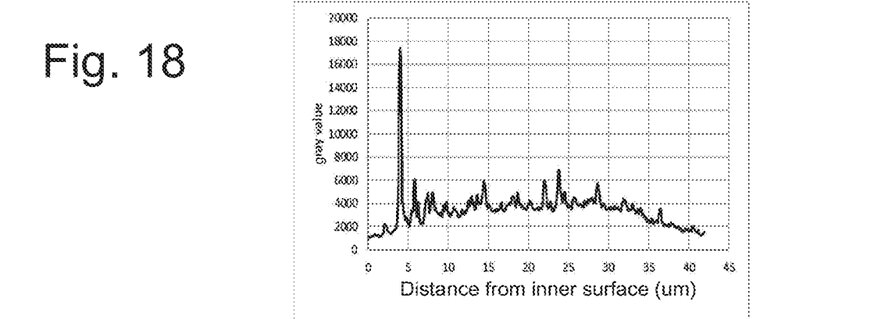
FIG. 18 is a line profile of a fluorescence intensity in the membrane thickness direction of the fluorescence microscopic observation image shown in FIG. 16. A distance from the inner surface is plotted along the abscissa and a gray value is plotted along the ordinate.
Figure 19:
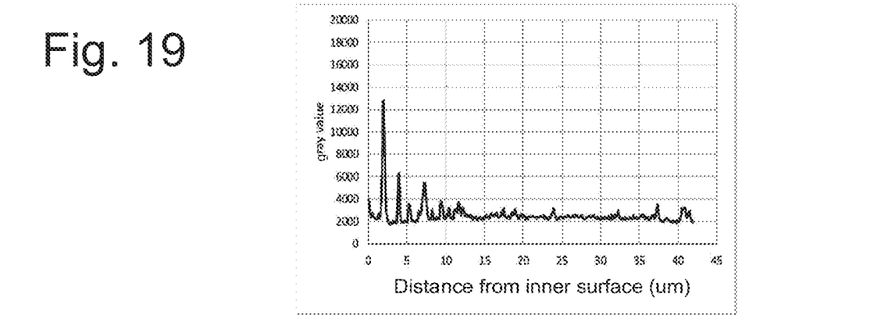
FIG. 19 is a line profile of a fluorescence intensity in the membrane thickness direction of the fluorescence microscopic observation image shown in FIG. 17. A distance from the inner surface is plotted along the abscissa and a gray value is plotted along the ordinate.

Sections (Comparative Examples 1-1 and 1-2, respectively) obtained from a filter similar to the virus removing filter used in Example 1-1 and Example 1-2 were stained with a goat polyclonal antibody against human immunoglobulin modified with FITC, a fluorescence material. The antibody stains both an aggregated protein and a non-aggregated protein. The sections were soaked in a 2% BSA/PBS-T solution at room temperature for 10 minutes for blocking. After washing, the antibody diluted to 100 times with a Dako antibody diluent buffer solution (Agilent Technologies) was added to the resulting sections. After the sections were reacted at room temperature for 60 minutes under light shielding, they were washed to remove the excess stain therefrom. Each washing was conducted four times with PBS-T. The sections after staining were subjected to fluorescence microscopic observation in a system similar to that of Example 1 except for the use of a 480/40-nm excitation filter, a 527/30-nm fluorescence filter, and a 505-nm dichroic mirror. Observation results are shown in FIG. 16 and FIG. 17. There is no large difference between Comparative Example 1-1 and Comparative Example 1-2 and rather, the fluorescence signal is slightly higher in Comparative Example 1-1 than in Comparative Example 1-2, showing the possibility that the existing amount of globulin is large. Fluorescence intensity line profiles of the images shown in FIG. 16 and FIG. 17 in the membrane thickness direction are shown in FIG. 18 and FIG. 19, respectively. Also from these drawings, no difference in fluorescence intensity was found between them. The aforesaid findings have revealed that the cause of the clogging of the membrane was not identified when a stain not specific to the aggregate was used.

Comparative Example 2

Figure 20:
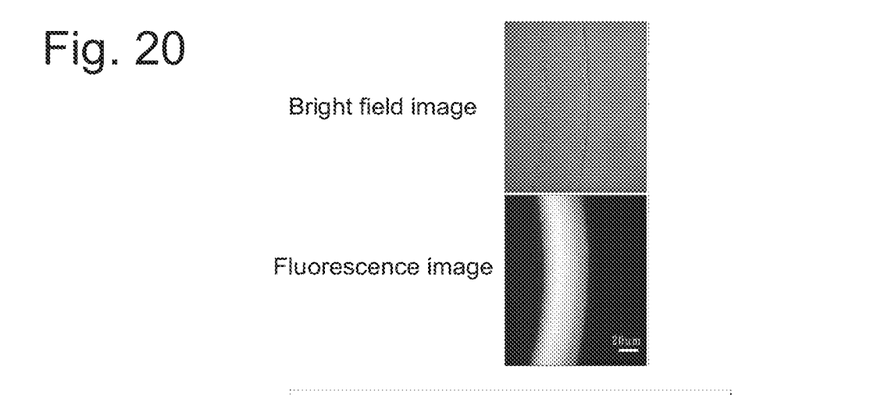
FIG. 20 is a fluorescence microscopic observation image of a virus removing filter stained with the fluorescence-labeled anti-globulin antibody according to Comparative Example 1-1.
Figure 21:
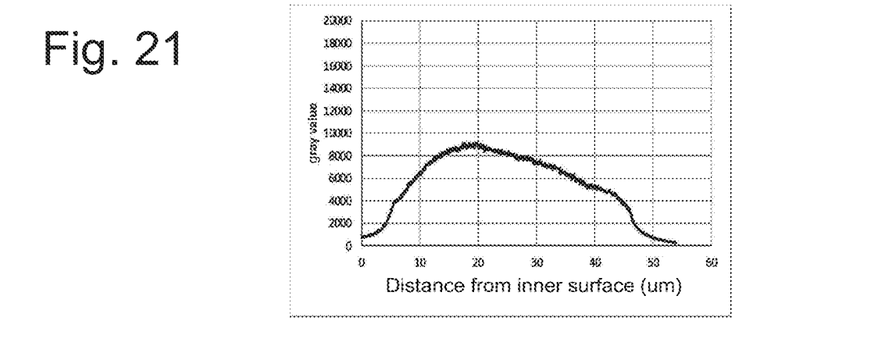
FIG. 21 is a line profile of a fluorescence intensity in the membrane thickness direction of the fluorescence microscopic observation image shown in FIG. 20. A distance from the inner surface is plotted along the abscissa and a gray value is plotted along the ordinate.

A section (Comparative Example 2) obtained from a filter similar to the virus removing filter used in Example 2 was stained and observed by an operation similar to that of Comparative Example 1. The image obtained as a result of the observation is shown in FIG. 20. A fluorescence intensity line profile in the membrane thickness direction obtained from the image of FIG. 20 is shown in FIG. 21. In the observation results, fluorescence was detected in the entire membrane thickness direction, but the whole protein was stained so that it was not determined from the results whether the aggregate was present or not.

What is claimed is:

1. A method for evaluating the clogging of a filtration membrane with a protein-containing solution, comprising the steps of:
    a) passing a protein-containing solution through a filtration membrane,
    b) after the step a), obtaining a filtration membrane cross-section from the filtration membrane,
    c) treating the protein-containing solution before the step a), the filtration membrane before the step b), or the filtration membrane cross-section after the step b) with at least one stain specific to an aggregate of the protein, and
    d) confirming the presence of the aggregate of the protein in the filtration membrane cross-section.

2. The method according to claim 1, further comprising, after the step a), a step of washing the filtration membrane.

3. The method according to claim 1, further comprising, after the step c), a step of washing the filtration membrane.

4. The method according to claim 1, further comprising a step of adding, to the filtration membrane, a stain which stains both the protein which has not aggregated and the protein which has aggregated.

5. The method according to claim 1, further comprising a step of fixing the filtration membrane cross-section.

6. The method according to claim 1, wherein the filtration membrane cross-section is a cross-section of a slice section of the filtration membrane.

7. The method according to claim 1, wherein the stain specific to the aggregate contains a material which specifically binds to an aggregation portion of the aggregate of the protein and thereby emitting fluorescence.

8. The method according to claim 7, wherein the stain specific to the aggregate is at least one selected from Nile red, Thioflavin T, and ProteoStat, and derivatives thereof.

9. The method according to claim 1, wherein the stain specific to an aggregate contains a binding material which specifically binds to an aggregation portion of the aggregate of the protein labeled with a fluorescent or luminescent material.

10. The method according to claim 9, wherein the binding material which specifically binds to the aggregation portion of the aggregate of the protein is at least one selected from an antibody, an antibody fragment, and a peptide.

11. The method according to claim 1, wherein the stain specific to an aggregate contains:
    (A) a primary binding material which specifically binds to the aggregation portion of the aggregate of the protein, and
    (B) a secondary binding material which specifically binds to the primary binding material and contains a detectable material.

12. The method according to claim 11, wherein the primary binding material is at least one selected from an antibody, an antibody fragment, and a peptide.

13. The method according to claim 11, wherein the secondary binding material is an antibody labeled with a fluorescent material.

14. The method according to claim 11,
    wherein the secondary binding material is an antibody modified with an enzyme, and
    the method further comprises, after the step c), a step of adding a substrate which will be decomposed by the enzyme into a fluorescent or luminescent material to the filtration membrane and detecting fluorescence or luminescence.

15. The method according to claim 14, wherein the enzyme is peroxidase or alkali phosphatase.

16. The method according to claim 1, wherein the filtration membrane is a virus removing membrane.

17. The method according to claim 1, further comprising, after the step c), a step of removing an unreacted stain specific to the aggregate.

18. The method according to claim 17, wherein the unreacted stain specific to the aggregate is removed by dialysis, ultrafiltration, or gel filtration.

* * * * *